United States Patent [19]
Burleigh

[11] Patent Number: 4,613,544
[45] Date of Patent: Sep. 23, 1986

[54] WATERPROOF, MOISTURE-VAPOR PERMEABLE SHEET MATERIAL AND METHOD OF MAKING THE SAME

[75] Inventor: Malcolm B. Burleigh, St. Paul, Minn.

[73] Assignee: Minnesota Mining and Manufacturing Co., St. Paul, Minn.

[21] Appl. No.: 677,982

[22] Filed: Dec. 4, 1984

[51] Int. Cl.⁴ .............................................. B32B 3/26
[52] U.S. Cl. ................................ 428/315.5; 427/245; 428/316.6; 428/422
[58] Field of Search ............... 428/315.5, 315.7, 315.9, 428/316.6, 422; 427/245

[56] References Cited

U.S. PATENT DOCUMENTS

| | | | |
|---|---|---|---|
| 3,265,529 | 8/1966 | Caldwell et al. | 428/264 |
| 3,326,713 | 6/1967 | Smith et al. | 428/264 |
| 3,852,090 | 12/1974 | Leonard et al. | 428/226 |
| 4,113,912 | 9/1978 | Okita | 428/315.5 |
| 4,194,041 | 3/1980 | Gore et al. | 428/422 |
| 4,344,999 | 8/1982 | Gohlke | 428/316.6 |
| 4,346,142 | 8/1982 | Lazear | 428/315.7 |
| 4,367,327 | 1/1983 | Holker et al. | 528/61 |
| 4,429,000 | 1/1984 | Naka et al. | 428/262 |
| 4,443,511 | 4/1984 | Worden et al. | 428/198 |
| 4,454,191 | 6/1984 | von Blucher et al. | 428/244 |
| 4,539,256 | 9/1985 | Shipman | 428/315.5 |

OTHER PUBLICATIONS

N. S. Schneider et al., *J. Macromol. Sci.-Phys.*, B3(4) 623–644, 767–766 (Dec., 1969).
J. L. Illinger et al, *Polymer Science and Technology*, vol. 6, 83–196, H. B. Hopfenberg, Plenum Press, New York and London (1974).
C. T. Chen et al., *J. Applied Polymer Science*, vol. 16, 2105–2114 (1972).

Primary Examiner—William J. Van Balen
Attorney, Agent, or Firm—Donald M. Sell; James A. Smith; Richard Francis

[57] ABSTRACT

A waterproof, moisture-vapor permeable unitary sheet material comprises a microporous polymeric matrix having pores comprising continuous passages extending through its thickness and opening into the opposite surfaces thereof, the passages being sufficiently filled with a moisture-vapor permeable, water-impermeable, hydrophilic material to prevent the passage of water and other liquids through the unitary sheet material while readily permitting moisture vapor transmission therethrough rendering the sheet material breathable. The unitary sheet is made by causing a liquid composition comprising the hydrophilic material or precursor thereof to flow into the pores of the matrix, then causing the conversion thereof to solid hydrophilic material.

15 Claims, 5 Drawing Figures

WATERPROOF, MOISTURE-VAPOR PERMEABLE SHEET MATERIAL AND METHOD OF MAKING THE SAME

DESCRIPTION

1. Technical Field

This invention relates to a waterproof, moisture-vapor permeable sheet material for use in clothing or other coverings for protecting against water and other liquids and to a method of making the same.

2. Background Art

The evolution of protective rainwear has seen the production of garments made of so-called "oil skins" (cloth impregnated with oil to make it waterproof), cloth impregnated or covered with hydrophobic polymeric material such as polyurethane or polyvinyl chloride, and plastic sheet material such as polyvinyl chloride or polyethylene sheet materials. Such materials, however, for the most part do not allow evaporation of perspiration.

Fabrics treated with hydrophobic liquids or polymeric materials such as silicone or fluorocarbon oil or resin are materials known to provide adequate evaporation of perspiration but they permit the passage of liquid water therethrough, commonly leaking when rubbed, touched or otherwise contacted or flexed.

U.S. Pat. No. 4,194,041 (Gore et al) is representative of a number of patents which describe coatings or laminates purported to provide waterproof articles which do not leak when touched and are breathable. This patent describes a layered article for use in waterproof garments or tents comprising at least two layers: an interior, continuous hydrophilic layer that readily allows water to diffuse therethrough, prevents the transport of surface active agents and contaminating substances such as those found in perspiration, and is substantially resistant to pressure induced flow of liquid water, and a hydrophobic layer that permits the transmission of water vapor and provides thermal insulating properties even when exposed to rain. The hydrophobic layer is preferably waterproof microporous tetrafluoroethylene (PTFE) or polypropylene, which permits the passage of moisture vapor through the pores thereof. The hydrophilic layer transfers moisture vapor therethrough whereupon it passes through the porous hydrophobic layer. Various means of joining the layers are suggested including the application of hydraulic pressure to force the hydrophilic polymer to penetrate into the surface void spaces of the hydrophobic layer.

U.S. Pat. No. 4,443,511 (Worden et al) discloses a layered article similar to that of U.S. Pat. No. 4,194,041, but formed of a breathable polytetrafluoroethylene first layer mechanically stretched at least about 5% beyond its yield point having a surface layer of elastomeric hydrophilic material having a surface in interlocking relationship with the inner face of the first layer. The interlocking relationship is said to be brought about by flowing the hydrophilic elastomeric material into the layer of hydrophobic material and then solidifying the hydrophilic material.

While these patents alleviate some of the problems known to the art, they require lamination and the attendent deficiencies created thereby, e.g., an exposed, weak hydrophilic layer subject to abrasion and separation and an exposed porous hydrophobic surface that is subject to contamination.

SUMMARY OF THE INVENTION

The present invention comprises a waterproof, moisture-vapor permeable, unitary, i.e., non-laminated and single thickness, sheet material that is ideally suited for use in waterproof garments, tents, and outdoor gear such as knapsacks and the like, combining exceptional durability with excellent hand or drape and a method of making the same.

This new unitary sheet material presents a continuous non-porous surface on each surface thereof which prevents water and other liquid penetration therethrough, in very thin thickness, e.g., 5 to 250 $\mu$m, even when the liquid is propelled thereagainst with great force, as in a rainstorm. The sheet material, while waterproof, is also very moisture-vapor permeable, being capable of constructions which allow moisture-vapor from perspiration to evaporate therethrough at a rate sufficient to maintain the skin of one wearing a garment containing the sheet material in a reasonably dry state with normal use, without, however, becoming contaminated with perspiration impurities which could otherwise cause eventual leakage through the sheet. Being unitary, the sheet material of this invention is very resistant to loss of its waterproof and moisture-vapor permeable properties through abrasion and rough wear as its properties are reasonably uniform throughout its thickness, being neither laminated nor otherwise applied in layers to provide these properties.

The waterproof, moisture-vapor permeable, unitary sheet material of this invention comprises a microporous matrix having pores comprising continuous passages extending through its thickness and opening into the opposite surfaces thereof, which passages are sufficiently filled with a moisture vapor permeable, water-impermeable, hydrophilic material to prevent the passage of water and other liquids therethrough while permitting the passage of moisture vapor therethrough. While the unitary sheet material can be tailored for varying rates of moisture-vapor permeability therethrough without disturbing the water-proofness thereof, a moisture vapor transmission rate (MVTR) of at least 1000 g/m² per 24 hours is preferred. The MVTR can be increased to 2000 g/m² or higher without significantly weakening the sheet material.

The term waterproof is used herein to describe sheet materials which are capable of preventing the passage therethrough of liquid water by capillary action and under varying natural atmospheric conditions including pressure driven flow as may be encountered in a rainstorm. Moisture vapor permeable is used herein to describe materials which readily permit the passage of water vapor therethrough but which do not allow the passage of liquid water therethrough. The term hydrophilic is used herein to describe materials, usually polymers, which are capable of absorbing water exposed thereto in significant quantity, typically more than about 10% by volume.

The invention also comprises a method of making a waterproof, moisture-vapor permeable, unitary sheet material which comprises the steps of providing a microporous polymeric matrix having continuous pores extending through its thickness, selecting a hydrophilic material, or precursor thereof which when converted to hydrophilic material, is moisture-vapor permeable and water-impermeable, preparing a liquid composition comprising said hydrophilic material or precursor thereof which wets the matrix polymer or, alternatively, rendering the polymeric surface of the matrix wettable to the liquid composition, causing the liquid composition to flow into the pores of the matrix, and causing the hydrophilic material or precursor thereof within the pores to convert to solid hydrophilic material thereby sufficiently filling the pore passage to close the pores against the passage of water through the unitary sheet material.

The presently preferred method of filling the micropores involves infiltrating a precursor of the hydrophilic material which wets the matrix polymer surface into the pores and in situ curing, e.g., polymerizing, the precursor to produce the hydrophilic material. A presently preferred precursor is a polyurethane prepolymer which includes a polyoxyethylene hydrophilic moiety. An alternative method involves infiltrating a solvent solution which contains the hydrophilic material and wets the matrix polymer surface into the pores and evaporating the solvent.

BRIEF DESCRIPTION OF DRAWINGS

The invention is further described and illustrated with reference to the drawings, wherein.

DETAILED DESCRIPTION

Figure 1:
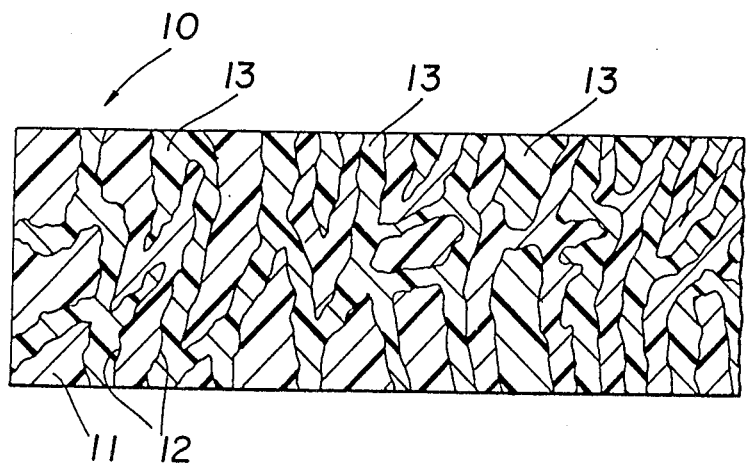
FIG. 1 is an enlarged sectional view of a unitary waterproof sheet material formed according to the present invention.

Referring now to the drawing, in particular FIG. 1, there is depicted a waterproof, unitary sheet material 10 prepared in accordance with the present invention. Sheet material 10 comprises microporous matrix 11 having continuous pores 12 extending through its thickness which are filled with a moisture-vapor permeable, water-impermeable, hydrophilic material 13.

In FIG. 1, the unitary sheet material is illustrated as a two phase, homogeneous unitary sheet material comprising the microporous matrix 11 as one phase and the hydrophilic material as the other phase.

The microporous matrix can be any material having continuous micropores through its thickness which can be filled with a liquid composition comprising the hydrophilic material or its precursor. While it is preferred that the entire area of a sheet material be microporous, sheets having solid, non-porous areas and microporous areas may be employed for particular applications. The pore size of the microporous matrix should be small to obtain uniform and adequate filling of the pores thought for the most part to occur by capillary action. The average size of the pores of the matrix is such that they are typically indistinguishable under magnification (e.g., 100×) of a conventional optical microscope but usually readily visible under magnification (e.g., 1000×) of an electron microscope. The pore size of a matrix will be much smaller than the matrix thickness. Preferably, the average pore size is less than about 10% of the thickness of the matrix. The average pore size for matrix having a thickness of about 10 to 50 μm will therefore typically be on the order of 1 to 5 μm, or less. By contrast, the average pore size or opening of a woven fabric is about the same magnitude as its thickness. A matrix which has a pore size which is too large can be readily identified as it will permit the passage of water therethrough as hydrophilic material solidified therewithin will not sufficiently close the pores against the passage of liquid therethrough. Useful microporous matrices have a void volume of about 10% to 85% or higher, preferably of at least 25% and more preferably from about 50%–85%.

The microporous polymeric matrix can be prepared by any known method of any polymeric material which is substantially impenetrable by water, i.e., absorbing no more than 5% by weight water under normal atmospheric conditions, and capable of forming such an article. Useful polymers for forming the microporous polymeric matrix include polyolefins such as polyethylene and polypropylene, polyethylenepolypropylene copolymers, polyethylene terephthalate, polycaprolactam, polyvinylidene fluoride, polybutylene terephthalate, polyester copolymer, and polytetrafluoroethylene. Any of these materials can be formed into a useful polymeric matrix by processes already known in the art. Polyolefins such as polyethylene are particularly preferred as they are tough, have excellent hand or drape and are easily wet by hydrophilic materials or precursors thereof useful in the practice of this invention.

The polymeric materials used to form the microporous matrices may, of course, include various other additive ingredients to impart specific properties to the product or as a process aid. For example, the polymeric material may include ultraviolet light stabilizers, bacteriostats, insect repellants, anti-static agents, coloring dyes, plasticizers, and the like. The polymeric materials may also include residues left from processing; however, these are usually in such small amounts they do not significantly adversely effect the final product.

Methods of preparing microporous matrices which are useful in the present invention are disclosed in U.S. Pat. No. 3,953,566 which discloses a process for making microporous sheets exclusively of polytetrafluoroethylene (PTFE) and Shipman (patent application Ser. No. 583,288, filed Feb. 28, 1984 now U.S. Pat. No. 4,539,256), assigned to the assignee of the present application, which discloses the preparation of microporous sheet materials from other thermoplastic polymers. The Shipman patent application disclosure is incorporated herein by reference.

The polymeric materials for the microporous matrices are preferably hydrophobic, but may also be hydrophilic, and they are useful so long as an infiltrate providing the hydrophilic material is capable of filling the pores and, when solidified, prevents the passage of water therethrough while allowing moisture vapor passage therethrough.

The selection of the polymer to form the microporous matrix will depend upon the ultimate product utility. For example, if the waterproof sheet material of the invention is to be used in the manufacture of waterproof clothing, flexibility and drape are desirable characteristics. Microporous polyethylene microporous matrices are therefore preferred for such use.

The hydrophilic materials useful in the present invention are polymeric substances which are typically void free but may contain closed cells. These materials do not allow the passage of gases or liquids through open channels or pores in the material but do transfer substantial amounts of water therethrough by absorbing water on one side of the material, where the moisture vapor concentration is high, and evaporating it on the opposite side where the moisture vapor concentration is low. Water is not transferred by capillary action or by wicking.

Films of the hydrophilic materials tend to be weak and easily torn, especially when swollen with water. Even if such films are laminated to strong support layers, they are still subject to abrasion and leakage. Infiltrating the hydrophilic material into a microporous matrix according to the present invention protects the hydrophilic material from abrasion without inhibiting its moisture vapor transmission properties and the combination often reinforces the microporous matrix to provide a sheet material which is stronger than its separate components in sheet form.

The hydrophilic material or its precursor must have an initial state which is liquid and which wets the matrix polymer surface in order for it to flow or be imbibed into the microporous media and it must be capable of being converted from the liquid state to a liquid-impermeable solid water vapor transport material which sticks to the passage walls of the pores of the matrix. Preferably, the hydrophilic material is prepared from a monomer or a prepolymer which can be infiltrated either neat or in solvent into the pores of the microporous media and in situ cured to form the hydrophilic material. The hydrophilic material may have a molten state which permits infiltraton, and a solid or semi-solid state when cooled. Solvent solutions of hydrophilic polymers may also be infiltrated and the solvent evaporated. Combinations of these techniques may also be used, e.g., infiltration of a solvent solution of a prepolymer and curing before or after solvent removal, e.g., by cross-linking. When solvents are used, care should be taken in the solvent selection to avoid adversely altering the microporous matrix. The same care should be taken when using other processing conditions such as heat.

The hydrophilic material will swell or expand in volume to a certain degree. The volume increase should not be so great as to distort the waterproof sheet material to an extent that would cause buckling or curling when the sheet material is attached to adjacent layers in a garment or other end product formation. It is preferred that the swellability (increase in volume), be less than 100% based on the original volume. Typically, the swellability is on the order of 35-75%.

The preferred hydrophilic material is polyethylene oxide sometimes referred to as polyoxyethylene. Polyethylene oxide is preferred because it remains in a softened or liquid state under ambient temperatures and it is reasonably resistant to degradation in typical use situations. The polyethylene oxide moiety may be present as a multifunctional derivative of a polymer containing other monomer units, depending upon the mode of synthesis, or it may be present as a copolymer with another alkylene oxide such as propylene oxide.

Polyethylene oxide is functionally an alcohol and it is preferably polymerized with a polyisocyanate to form a polyurethane. The moisture vapor transmission rate of polyoxyethylene urethanes may be controlled by varying the proportion of polyethylene oxide. The polyethylene oxide moiety forms a separate phase within the urethane polymer through which the moisture vapor transmission rate will vary in proportion to the polyethylene oxide content but not necessarily in a linear manner. The polyethylene oxide content is preferably greater than 10% by weight in the urethane polymer to obtain preferred moisture vapor transmission rates of at least 1000 $g/m^2$ per 24 hours. A commercially available hydrophilic material that embodies the requisite hydrophilic properties for use in the invention is obtained by curing a hydrophilic polyurethane prepolymer sold under the registered trademark "Hypol", preferably "Hypol" FHP 2000, by W. R. Grace & Co. "Hypol" is the trademark of a reactive polyurethane prepolymer that can be crosslinked by water, multifunctional amines and polyols, to produce a crosslinked hydrophilic polymer. This prepolymer has a polyoxyethylene backbone and terminal toluene diisocyanate units each having an available unreacted NCO group.

The hydrophilic material may include various additive ingredients which do not effect the water vapor transmissive properties or its ability to prevent passage of liquid water. Examples of additive materials include ultraviolet light stabilizers, bacteriostats, insect repellants, anti-static agents, and the like.

The moisture vapor transmission characteristics of the waterproof sheet material of the invention are governed by the thickness of the sheet and the composition of the hydrophilic material. Generally, the moisture vapor transmission rate varies inversely with the thickness of the sheet, i.e., with thicker waterproof sheets having lower moisture vapor transmission rates. Preferred sheet materials according to the invention have a thickness on the order of 5 to 250 micrometers, most preferably 5 to 150 micrometers.

A vapor pressure differential between opposite sides of the sheet promotes moisture vapor transmission through the sheet. Thus, when the sheet material of the invention is used in a rain garment, the wearer is maintained in a dry condition under exterior wet or rainy conditions because of the difference in water vapor pressure with temperature between the exterior of the garment and its interior, i.e., the area near the body. The surface insulative value of the sheet material of the invention in the garment creates a temperature difference between the inside of the garment and the outside to provide the vapor pressure differential which promotes moisture vapor transmission from the wearer to the outside of the garment and keeps the wearer dry. If the wearer generates more moisture than can be transmitted through the sheet, e.g., by exercise, it may be desirable to include a layer of water sorbent material on the interior of the garment, next to the wearer. Suitable sorbent materials include webs of polymeric fibers. Such webs may also provide additional insulation for warmth. A preferred insulating material which can be used to form a layered construction with the sheet material of the invention is sold under the trademark "Thinsulate" by the Minnesota Mining and Manufacturing Company.

It is preferred to employ the sheet material of the present invention as the inside layer of a garment with a preferably stronger exterior layer. It is undesirable for the exterior layer to become wet. Therefore, the exterior layer is preferably a breathable fabric which is treated to be water-repellant. Fabrics for use as the exterior layer include tightly woven fabrics of fine hydrophobic fibers including polyolefin fibers such as polyethylene and polypropylene, nylon, blends of such fibers with natural fibers such as cotton and other fibers, any of which may be treated with water repellants. Preferred fabrics for the exterior of a layered construction include nylon cloths such as nylon tricot and cloth available under the trademarks "Taslin" or "Ripstop", cotton/polyester blends and the like. Suitable water repellant materials for treatment of the exterior fabric are commercially available, for example, under the trademarks "Scotchgard" or "Zepel".

The unitary sheet materials of the present invention are conveniently prepared by applying to the surface of the microporous matrix a liquid, curable composition comprising a precursor of the hydrophilic material or the hydrophilic material itself, as previously explained. Such compositions may be conveniently applied to the matrix by rotogravure coating devices, padding operations, dipping techniques, spraying, or other conventional coating techniques. Depending upon the microporous matrix, it may easily imbibe the coating composition or it may require preparation prior to coating. Viscosity adjustment of the coating composition may be needed in some cases to obtain good penetration by capilliary action into the pores. In some cases it may be necessary to treat the surface of the microporous matrix to make it more receptive to imbibing the coating composition. For example, a microporous polytetrafluoroethylene matrix may be pre-wet with tetrahydrofuran to make it more receptive to solvent solutions which do not readily wet its surface.

It is preferred that the coating operation sufficiently fills the pores of the microporous matrix without leaving substantial quantities of the hydrophilic material on either exterior surface of the completed unitary sheet material. While minor amounts of hydrophilic material on the surface of the sheet are not detrimental, excessive amounts may inhibit moisture vapor transmission, and may also weaken laminates made of the unitary sheet material and other materials because the hydrophilic material typically has a lower cohesive integrity than that of the microporous matrix. Lamination of other sheet materials or fabrics directly to the unitary sheet material, rather than to a surface layer of hydrophilic material, will therefore provide a more delamination-resistant article.

The conditions under which the hydrophilic material or precursor is solidified will depend upon the particular type of liquid composition. Compositions which comprise the hydrophilic material in a solvent will require solvent removal which may be accomplished with the aid of moderate heating. Hydrophilic materials, which are formed from curable precursors are cured under appropriate curing conditions, depending upon the particular precursor. Monomeric materials and prepolymers are cured according to the requisite curing conditions, usually requiring heat or light.

The resultant waterproof, moisture-vapor permeable sheet material is useful for making any of a variety of products. Examples of such products include garments such as rain coats, skiing apparel, snowmobile suits, snowsuits, gloves, shoes, garments to be worn in areas where chemical spills may be encountered, clean room garments, and the like. The sheet material of the invention may also be utilized in medical applications as a wound dressing. The sheet material may also be used to make tents and other types of camping equipment.

For such uses, the sheet material is typically cut to form pieces which are sewn to form a garment, preferably taking care to prevent leakage at the seams by conventional techniques. Wound dressings are typically sterilized prior to use according to conventional techniques and may include other modifications such as absorbent pads and medicaments.

EXAMPLES

The invention is illustrated by the following examples, wherein all parts are by weight unless otherwise stated.

HYDROPHILIC MATERIAL SOLUTIONS

The following solutions were prepared by mixing the below designated ingredients without regard to order of addition with a 3-blade laboratory mixer under ambient conditions.

| Parts | Ingredient |
|---|---|
| | Solution A |
| 800 | Polyurethane prepolymer having an equivalent weight of 625 per NCO group, density of 1.19 g/ml at 25° C., a viscosity of 10,000–15,000 cps at 25° C. and an NCO content of 1.95–2.20, and being available under the registered trademark "Hypol" FHP 2000 from W. R. Grace Co. |
| 300 | Difunctional polyoxyethylene end-capped with hydroxyl groups, having a molecular weight of 600 and being available under the registered trademark "Carbowax" 600 from the Union Carbide Co. |
| 1100 | Methyl ethyl ketone |
| 20 | Dibutyl tin dilaurate as a 2% by weight solution in toluene |
| | Solution B |
| 300 | Difunctional polyoxyethylene available under the registered trademark "Carbowax" 600. |
| 140 | Polyfunctional methylene biphenyl isocyanate having an equivalent weight of 138 and an average functionality of 2.7, and being available under the registered trademark "Mondur" MRS from the Mobay Co. |
| 440 | Toluene |
| 10 | Dibutyl tin dilaurate as a 2% by weight solution in toluene |

EXAMPLE 1

This example illustrates the preparation of a unitary sheet material from a microporous polyethylene matrix and a polyurethane-polyoxyethylene hydrophilic material.

The microporous matrix was prepared by first extruding through a film die a melt blend of 54% by weight mineral oil and 46% by weight polyethylene that had been heated until the mineral oil and polyethylene were miscible, depositing the extruded film into a quench bath where the polyethylene phase separated from the mineral oil to create distinct particles of polyethylene with oil between the particles but having points of continuity between adjacent particles, thus producing a quenched film having an average caliper of 84 micrometers. The quenched film was washed with 1,1,1-trichloroethane to remove substantially all of the mineral oil, leaving less than 2% by weight mineral oil based on the weight of the film. The oil-extracted film was then length oriented and tentered by a factor of 2.5 both in the machine (down) and in the transverse (cross) directions to attenuate the polyethylene at the points of continuity to form fibrils and provide porosity. The length orientation temperature was 65° C. and the transverse orientation temperature was first 65° C. and then 93° C. The resultant oriented film had an average caliper of 30 micrometers, a weight of 7 g/m², a void volume of 79%, and a porosity measured by a Gurley Porosimeter of 12 seconds/50 ml.

The pore passages of the microporous matrix film were filled with Solution A by first placing the matrix film on a silicone release liner, and then passing the film on the liner through a rotogravure press equipped with a 16 line/cm ruling mill by means of which Solution A was infiltrated into the matrix pore passages. The infiltrate in the microporous sheet was then cured by heating at 110°–115° C. for 5 minutes in a continuous-pass oven to produce a cured dry hydrophilic material add on weight to the matrix of 36 g/m². The physical properties of the resultant waterproof unitary sheet material are shown in the Table following these examples.

EXAMPLE 2

This example illustrates the use of a microporous polytetrafluoroethylene (PTFE) matrix in making the unitary sheet material of the invention. A PTFE microporous, having a weight of 23 g/m², a thickness of 51 micrometers, a void volume of 65% and a Gurley porosity of 5.7 sec/50 ml and marketed under the registered trademark, "GORE-TEX", was used as the polymeric matrix. The matrix film was placed on a silicone release liner and the matrix and liner were fed into a rotogravure press equipped with a 13 line/cm ruling mill where Solution B, which is a solvent solution of hydrophilic material precursor was infiltrated into the matrix pore passages. The infiltrate was cured to a solid hydrophilic material within the pore passages by heating for 5 minutes at 130° C. in a continuous-pass oven to form the resultant unitary sheet. Results of physical testing are shown in the Table.

EXAMPLE 3

This example illustrates the use of a low water absorptive microporous polymeric matrix in the preparation of the sheet material of the invention. A hydrophilic material forming solution was prepared by mixing with a three blade mixer attached to a laboratory mixer motor 50 parts by weight polyurethane prepolymer ("Hypol" FHP 2000) dissolved in 100 grams methyl-ethyl ketone. The solution was infiltrated into the matrix pores by swab-coating it on to the surface of a hydrophilic microporous polyamide matrix (the polyamide being available under the registered trademark "Foster Grant" nylon 438) film. The microporous polyamide matrix was prepared in a similar manner to that described in Example 1 according to aforementioned Shipman patent application Ser. No. 583,288, filed Feb. 28, 1984, had an average caliper of 89 microns, a void volume of 16% and a Gurley porosity of 1355 sec/50 ml. The solution lodged in the pores of the matrix was then precured by heating for 5 minutes in a 93° C. oven, then allowed to fully cure to a solid hydrophilic product at room temperature for approximately 12 hours to produce a unitary sheet. The results of physical testing are shown in the Table.

EXAMPLES 4 and 5

Examples 4 and 5 illustrate the use of a hydrophilic polyurethane which is not cross-linked but instead is simply impregnated and then dried to a solid hydrophilic material in the microporous matrix to form a unitary sheet. Example 5 also illustrates pretreatment of the microporous matrix to facilitate flowing of a solution which does not easily wet the matrix polymer into the pores of the matrix.

Diethylene glycol (35.8 g) and 77.1 g difunctional polyoxyethylene end-capped with hydroxyl groups having a molecular weight of 1000, (available under the registered trademark "Carbowax" 1000 from the Union Carbide Company), were dissolved in 350 ml dichloromethane and this mixture was added dropwise over a period of 4 hours to a mixture of 107.5 g methylene biscyclohexyldiisocyanate, (available under the registered trademark "Desmodur" W from the Mobay Chemical Corporation), 1.2 g dibutyl tin dilaurate and 125 ml dichloromethane. This reaction mixture was allowed to stand overnight and was then refluxed with stirring for 2 hours. Ethylene glycol (25 g) and an additional 2 g of dibutyl tin dilaurate were then added and the mixture allowed to react for another 2 hours.

The mixture was then dried for an additional 2 hours at 65° C. in a flat aluminum pan and the resultant solid product was dissolved in 2 liters of ethanol. This solution was then poured into 2 liters of water, forming an emulsion which was broken by briefly heating. The resultant resin was collected, placed into flat aluminum pans and dried at 65° C. for 8 hours to provide a solid hydrophilic material.

An infiltrate solution was prepared by dissolving the resin in dimethylformamide to make a 20% by weight solids solution, this solution was then poured onto the surface of a microporous polymeric matrix and spread evenly thereover with a cotton pad for infiltration into the pore passages of the matrix.

The matrix film of the sheet of Example 4 was the microporous polyethylene matrix film described in Example 1. The microporous polymeric matrix used for Example 5 was the PTFE matrix film described in Example 2. The PTFE matrix required prewetting with tetrahydrofuran before applying the hydrophilic solution to overcome the hydrophobic surface properties of the PTFE. The resulting unitary sheet material was dried at 115° C. for 15 minutes to solidify the hydrophilic material in the pores. Results of physical testing are shown in the Table.

EXAMPLES 6 and 7

Examples 6 and 7 exemplify the use of non-urethane hydrophilic materials in waterproof unitary sheet materials according to the present invention. Example 6 includes a hydrophilic material which is a polyester with polyoxyethylene in its backbone. Example 7 includes a hydrophilic material which is a cross-linked polyvinyl alcohol.

Example 6 was prepared by stretching a polyethylene microporous matrix film of the type described in Example 1 over a frame. The stretched matrix then had applied over one surface thereof a solution consisting of 20 parts by weight of styrene-maleic anhydride copolymer (available under the trade designation "FMA"-1000A from the Arco Chemical Company), as a 20% by weight solution in dimethylformamide, 10 parts bifunctional polyoxyethylene end-capped with dihydroxy groups having a molecular weight of 1000 from the Union Carbide Company) and 0.1 part methanesulfonic acid. The solution was spread uniformly over a surface of the microporous matrix and permitted to soak into the pores thereof. The solution was then cured by heating for 35 minutes at 115° C. to form a solid hydrophilic material closing the pores and produce the waterproof unitary sheet material according to the present invention. The unitary sheet material had a moisture vapor transmission rate of 7,900 g/m$^2$ 24 hours.

Example 7 was prepared in the same manner as Example 6 except the solution consisted of 20 parts polyvinyl alcohol, being obtained as a 75% hydrolyzate of polyvinyl acetate and having a molecular weight of 2,000 (available from Aldrich Chemical Company under the designation 18,936-7) dissolved in 1-methyl 2-pyrrolidinone to make a 20% by weight solution and 0.1 part methanesulfonic acid. The solution was cured to a solid hydrophilic pore closing material by heating at 115° C. for 15 minutes, producing a waterproof unitary sheet material according to the present invention having a moisture vapor transmission rate of 5,700 g/m$^2$ 24 hours.

EXAMPLE 8

This example illustrates the use of a microporous polypropylene matrix sheet a film in the preparation of a unitary sheet material according to the invention. A commercially available microporous polypropylene sheet material sold under the registered trademark "Celgard" by the Celanese Plastics Company having a 33% void volume was used as the polymeric matrix. This solution was infiltrated into the pore passages of the matrix by swab-coating the matrix with Solution B over the surface thereof while the matrix was stretched over a frame. The solution was cured to a solid hydrophilic material closing the pores of the matrix by heating for 15 minutes at 145° C. Results of physical testing of the resultant waterproof sheet material are shown in the Table.

CONTROL EXAMPLE

Example VI of U.S. Pat. No. 4,194,041 was repeated by coating a fillet of "Hypol" FHP 2000 polyurethane prepolymer (described above) onto the surface of a PTFE membrane of the type described in Example 2 which had been taped to a work bench. A 13 line/cm "Mayer" bar (a wire wound rod) was used to apply the prepolymer as a coating over the PTFE membrane. The bar was repeatedly passed back and forth over the PTFE surface to work the prepolymer into the membrane. This coated sample was then passed at 50 cm/min between two 15 cm diameter nip rolls at a nip pressure of $6.9 \times 10^{55}$ dynes/cm$^2$. A piece of nylon tricot cloth that had been fully wet with water was then placed over the coating on the membrane and the prepolymer was allowed to partially cure for 5 minutes at room temperature. The coated membrane was removed from the bench, placed into a 65° C. oven and heated for about 20 minutes until the nylon tricot cloth had dried.

Figure 5:
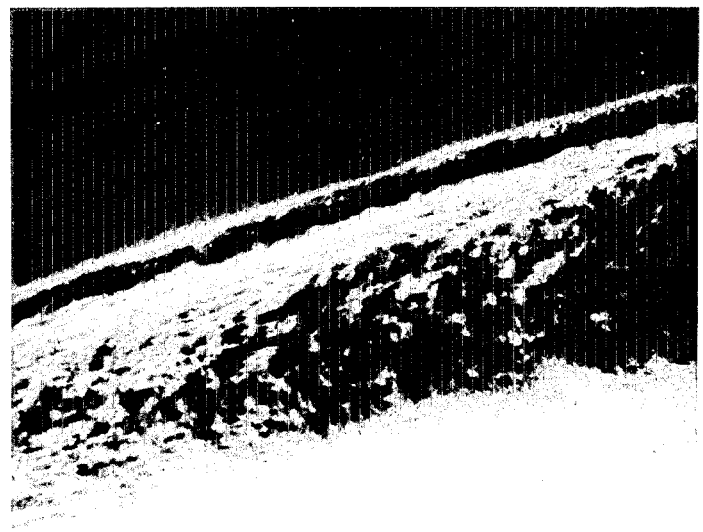
FIG. 5 is a 2000× photomicrograph of the cut end of a sheet material made in accordance with Example VI of U.S. Pat. No. 4,194,041 (Gore et al).

The resultant coated membrane was cut with a razor to show sectional detail and photomicrographed with results shown in FIG. 5. As shown, the light fibrous structure is the PTFE membrane while the darker portion of the photomicrograph is the coating of hydrophilic polyurethane from the "Hypol" FHP 2000. The very dark heavy line below a narrower light line is a fracture in the PTFE web caused by cutting the sheet material to prepare this sample. The narrower lighter line above the fracture shows minor surface penetration into the PTFE sheet by the hydrophilic polyurecthane coating.

PHYSICAL TESTING

Procedures used for physical testing are described below.

POROSITY TEST

The test for air porosity was ASTM D72658 which test employs a "Gurley" densometer manufactured by W. and L.E. Gurley and Sons. Results are reported as a "Gurley" number which is the time in seconds for 50 ml of air to pass through one square inch (about 6.5 cm$^2$) of the sample under a pressure of 4.9 inches (124 mm) of water. Useful microporous films have been found to have a Gurley Number of 5–1400, preferably 5–1000, sec/50 ml. Liquidproof sheet materials according to the invention are nonporous, i.e., have an infinite Gurley number.

MOISTURE VAPOR TRANSMISSION TEST

The method for determining moisture vapor transmission rates employs apparatus described in ASTM E96-B66B, but has been modified as disclosed in U.S. Pat. No. 4,194,041. ASTM E96-B66B employs a tapered polypropylene cup which is 11.5 cm high with a 8.2 cm diameter mouth over which the sample to be tested is fastened after first filling the cup with approximately 160 cc of water. This creates an air gap between the surface of the water and the sample to be tested. Such an arrangement would provide an estimated moisture vapor transmission rate of about 900 g/m$^2$ day. Thus, using the unmodified test for determining the moisture vapor transmission rate of materials with very high rates of the type described in the present application provides misleading results, unless modification is made.

Modification involves inverting the cup to eliminate the air gap by bringing the water directly in contact with the surface of the test material. Such a modification is acceptable since the materials being tested made in accordance with the present invention are waterproof.

The test is conducted by filling the cup with 160 cc of water, sealing the sample being tested to the lip of the cup with silicone adhesive, weighing the cup and its contents including the attached sample to the nearest 1/100 gram and placing the cup in a rubber collar under tension beneath the lip at the mouth of the cup. The assembly is then suspended upside down through a circular opening in a support plate in an environmental chamber so that the sample is disposed 10 cm above the bottom surface of the chamber. The chamber is held at a temperature of about 24° C. and a relative humidity of 40% and a linear air flow of 250 cm/sec. is directed through the air space between the bottom of the chamber and across the surface of the sample being tested. The sample is permitted to remain in this position for a 15 hour period, then removed and reweighed within 1/100 of a gram. The moisture vapor transmission rate is then reported in g/m$^2$ for a 24 hour period.

Useful waterproof sheet materials according to the present invention have a moisture vapor transmission rate of at least 1000, preferably at least 2000, g/m$^2$ per 24 hours.

TENSILE STRENGTH AND ELONGATION

The tensile strength of the samples was measured using a die-cut dumbbell-shaped test specimen which was 3.2 cm long by 0.63 cm wide except for the ends which were wider for grasping in the jaws of an "Instron" tensile strength testing device. The jaws were set 7.6 cm apart and operated at a crosshead speed of 25.4 cm/min. until the maximum tensile strength was achieved just before breaking. The maximum tensile strength at break and the amount of stretch or elongation in centimeters at break were measured. Samples were tested "ambient", i.e., equilibrated under ambient room temperature (about 23° C.) and humidity (about 50% relative humidity) conditions, and "hydrated" by first wrapping the test sample in a wet paper tissue for at least 3 but not more than 4 minutes before the test.

ABRASION RESISTANCE

A waterproof unitary sheet material made in accordance with the present invention and a waterproof sheet material made in accordance with Gore (U.S. Pat. No.4,194,041) were tested for abrasion resistance by using a double-head "Taber" abrasion resistance testing device according to the Taber test method (also known as Federal Test Standard No. 191A, Method 5306). The Taber method is known for determining the abrasion resistance of various sheet materials such as cloth in terms of percent change in breaking strength after a given period of abrasion or a given number of abrasion cycles required to produce a specified state of destruction. In the present case, the method was utilized to determine the number of abrasion cycles that had elapsed until the waterproof component of the sample being tested perforated so that it was no longer leakproof but permitted the passage of liquid.

The double-head Taber abrasor is a commercially available device that has a removable flap circular sample holder, a pair of pivoted arms which are attached to abrasive wheels, a motor for rotating a sample platform carrying the sample holder, a fan for cooling the motor, and a counter for indicating the number of abrasion cycles of the sample holder. The sample holder is mounted so that the sample travels in a circular path. Opposed abrasive wheels attached to the free ends of the pivoted arms rest on the sample as it rotates with the periphery of the abrasive wheels in contact with the surface of the sample at an acute angle. Hard felt type CS-5 abrasive wheels weighted at 250 g were used.

The sample according to the Gore patent was a "Gore-Tex" waterproof membrane/nylon cloth laminate (the nylon cloth being available under the trademark "Taslin"). The sample according to the present application was the unitary sheet material of Example 1 laminated to nylon cloth available under the trademark "Ripstop".

The test involved placing the test sample on the sample holder with the waterproof membrane in contact with the abrasive wheels and rotating the sample holder in cycles of 10 rotations each until leakage was detected through the sample. Leakage testing was conducted after each 10-rotation cycle. Leakage was detected by wetting one surface of the membrane with ethanol and observing if the ethanol leaked through or wet the opposite surface.

The "Gore-Tex"/nylon cloth sample, tested with its hydrophilic surface layer in contact with the abrasive wheel, started to leak after 70 cycles. By contrast, the sample according to the present invention had not commenced leakage after 1,000 cycles, clearly indicating the superiority of the materials according to the present invention.

MULLEN BURST TEST

Figure 4:
FIG. 4 is a 1500× photomicrograph of the cut end of a commercially available waterproof laminated sheet material sold under the trademark "Gore-Tex"

The unitary sheet material according to the present invention was evaluated for waterproofness by the so-called Mullen Burst Test which is also known as Federal Standard 191 Method 5512. The test utilizes apparatus depicted in FIG. 4 of U.S. Pat. No. 4,194,041. The apparatus consists of a water-filled chamber which is open at its mouth which includes a holder to hold a sheet of the material being tested, a piston and cylinder arrangement which forces water into the chamber to apply pressure on the sample being tested, and a pressure gauge for measuring the water pressure in the system. The sheet material laminated to a woven fabric is tested with the woven fabric on the low pressure side and the sheet material of the invention on the high pressure side to determine the burst pressure or the pressure at which the sheet material of the invention commences rapid failure and leakage, this being reported in dynes/cm in the Table. Useful liquidproof materials preferably have a Mullen burst value of at least $3 \times 10^6$ dynes/cm.

LIQUID PROOFNESS TEST

Figure 3:
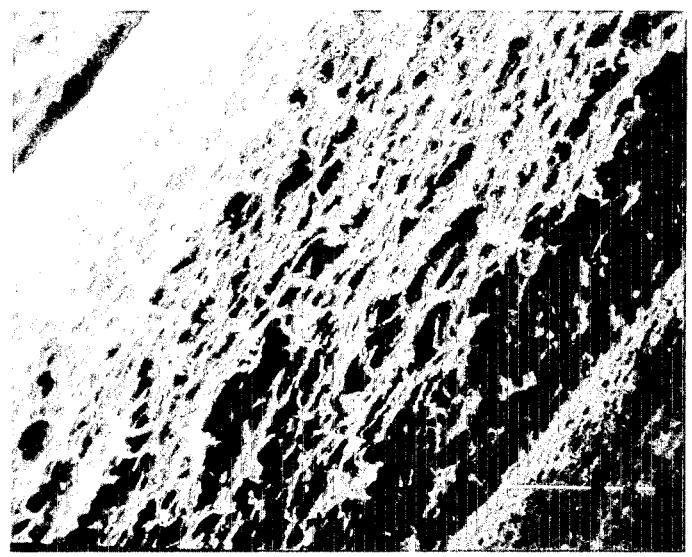
FIG. 3 is a 1500× photomicrograph of the end of the microporous polyethylene matrix of the waterproof unitary sheet material depicted in FIG. 2.
Figure 2:
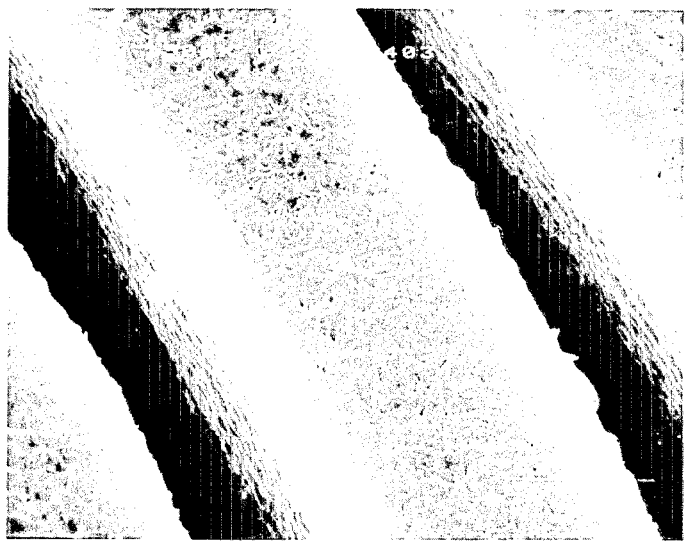
FIG. 2 is a 1500× photomicrograph showing a perspective view of the cut ends of three separated layers of a unitary waterproof sheet material made in accordance with the present invention, the two inclined dark bands being spaces between layers.

Films of the present invention were tested and found to be liquidproof for liquids other than water. The testing device employed was that depicted in FIG. 3 of U.S. Pat. No. 4,194,041 which included a cylindrical container with a gasket-lined mouth, an air-vented removable cup-shaped clear plastic top with a gasket-lined mouth, a clamp to hold the top in place during testing, and an open-ended tube extending at a right angle to the container wall and then vertically to a height which exceeded that of the container.

A test film sample was placed over the mouth of the liquid filled container and the top clamped in place, securing the film sample between the gaskets in a leak-proof seal so that one side of the test film was in contact with the liquid in the container while the other side was exposed to a cavity formed by the top. The test liquid was then placed into the tube until a pressure head equivalent to at least 250 mm of mercury was achieved and maintained for at least 15 minutes. Leaks were determined by visual inspection of the side of the test sample facing the top.

A laminate of nylon "Ripstop" cloth and the moisture vapor permeable liquidproof film of Example 1, with the cloth side of the laminate facing the top of the device, was tested as described above. No liquid leakage was noted in separate tests using as test liquids toluene, ethanol, and methylethyl ketone.

TABLE

| Sheet Material | Tensile Strength (g/0.63 cm) | | Elongation (cm) | | Sheet Thickness (μm) | Sheet Wt. (g/m²) | Gurley Porosity (sec/50 ml) | Moisture Vapor Transmission Rate (g/m² 24 hours) | Mullen Burst Test (× 10⁶ dynes/cm²) |
|---|---|---|---|---|---|---|---|---|---|
| | Cross | Down | Cross | Down | | | | | |
| Microporous polyethylene | 110 | 165 | 3.8 | 6.3 | 30 | 7 | 11.7 | 9,800 | 7.2 |
| Ex. 1 | 430 | 460 | 11.9 | 10.9 | 33 | 43 | ∞ | 10,000 | 7.9 |

TABLE-continued

| Sheet Material | Tensile Strength (g/0.63 cm) Cross | Down | Elongation (cm) Cross | Down | Sheet Thickness (μm) | Sheet Wt. (g/m²) | Gurley Porosity (sec/50 ml) | Moisture Vapor Transmission Rate (g/m² 24 hours) | Mullen Burst Test (× 10⁶ dynes/cm²) |
|---|---|---|---|---|---|---|---|---|---|
| Ex. 1 (ambient) | 350 | 400 | 6.3 | 6.6 | — | — | ∞ | — | — |
| Ex. 1 (hydrated) | 400 | 220 | 5.0 | 10.0 | | | | | |
| Microporous PTFE | | | | | 18 | 14 | 5.7 | 13,600 | — |
| Ex. 2 (ambient) | 450 | 310 | 5.0 | 11.5 | 18 | 38 | ∞ | 12,600 | 7.2 |
| Ex. 2 (hydrated) | 500 | 310 | 4.5 | 8.0 | — | — | ∞ | — | — |
| Microporous polyamide | — | — | — | — | 89 | 88 | 1355 | — | — |
| Ex. 3 (ambient) | — | — | — | — | 89 | 108 | ∞ | 1,400 | — |
| Ex. 4 (ambient) | — | — | — | — | — | — | — | 7,325 | — |
| Ex. 5 (ambient) | — | — | — | — | — | — | ∞ | 15,100 | — |
| "Celgard" film | 270 | 1680 | 1 | 1 | 25 | 15 | 385 | 7,800 | 9.2 |
| Ex. 8 (ambient) | 320 | 1100 | 2 | 1 | 25 | 25 | ∞ | 2,100 | 8.8 |
| Ex. 8 (hydrated) | 320 | 1200 | 0.5 | 1 | — | — | ∞ | — | — |

I claim:

1. A waterproof, moisture-vapor permeable unitary sheet material comprising a microporous polymeric matrix having continuous pores comprising continuous passages extending through its thickness and opening into both surfaces thereof, said pores being sufficiently filled with a moisture-vapor permeable, water-impermeable, hydrophilic material to prevent the passage of water through said unitary sheet material.

2. The unitary sheet material of claim 1 wherein the polymeric material forming said microporous polymeric matrix is a polyolefin.

3. The unitary sheet material of claim 2 wherein said polyolefin is a member selected from the group consisting of polyethylene and polypropylene.

4. The unitary sheet material of claim 1 wherein the polymeric material forming said microporous polymeric matrix is polytetrafluoroethylene.

5. The unitary sheet material of claim 1 having a moisture vapor transmission rate of at least 1000 g/m² per 24 hours.

6. The unitary sheet material of claim 1 having a thickness of about 5 to 250 micrometers.

7. The unitary sheet material of claim 1 wherein said hydrophilic material is a polyurethane comprising a polyoxyethylene backbone.

8. A laminate comprising the sheet material of claim 1 and fabric.

9. A garment comprising the laminate of claim 8.

10. A wound dressing comprised of the sheet material of claim 1.

11. A two phase, homogeneous, waterproof, moisture-vapor permeable, unitary sheet material comprising a microporous polymeric first phase having pores comprising continuous passages opening into the opposite surfaces thereof, and a second phase comprising moisture-vapor permeable, water impermeable, hydrophilic material sufficiently filling said pores to prevent the passage of water through said unitary sheet material.

12. Method of making a waterproof, moisture-vapor permeable unitary sheet material, said method comprising the steps of:
  (a) providing a microporous polymeric matrix having pores extending through its thickness;
  (b) selecting a hydrophilic material or precursor thereof which when converted to said hydrophilic material is moisture-vapor permeable and water-impermeable;
  (c) preparing a liquid composition comprising said hydrophilic material or a precursor thereof for flowing into the pores of said matrix;
  (d) if needed, rendering the polymeric surface of said matrix wettable to said liquid composition;
  (e) causing the liquid composition to flow into the pores of said matrix; and
  (f) causing said hydrophilic material or precursor thereof to convert to solid hydrophilic material within said pores to sufficiently fill said pores to prevent the passage of water through said unitary sheet material.

13. The method of claim 12 wherein said liquid composition comprises a precursor of said hydrophilic material and said causing to convert comprises in situ polymerizing said precursor to produce said solid hydrophilic material.

14. The method of claim 13 wherein said precursor is a polyurethane polyoxyethylene prepolymer.

15. The method of claim 12 wherein said liquid composition comprises a solvent solution of said hydrophilic material and said causing to convert comprises evaporating said solvent.

* * * * *

UNITED STATES PATENT AND TRADEMARK OFFICE
CERTIFICATE OF CORRECTION

PATENT NO. : 4,613,544
DATED : September 23, 1986
INVENTOR(S) : MALCOLM B. BURLEIGH It is certified that error appears in the above-identified patent and that said Letters Patent is hereby corrected as shown below:

In the Specification:

Col. 11, line 49, "$6.9 \times 10^{55}$ dynes/cm$^2$" should read --$6.9 \times 10^{5}$ dynes/cm$^2$--.

Col. 11, line 67, "polyurecthane" should read --polyurethane--.

Signed and Sealed this

Thirty-first Day of March, 1987

Attest:

DONALD J. QUIGG

Attesting Officer

Commissioner of Patents and Trademarks